United States Patent [19]

Sansur et al.

[11] 4,119,401
[45] Oct. 10, 1978

[54] TOTAL BILIRUBIN ASSAY

[75] Inventors: Musa M. Sansur, Eastchester; Daniel L. Vlastelica, Congers; Anne C. Delea, Yonkers, all of N.Y.

[73] Assignee: Technicon Instruments Corporation, Tarrytown, N.Y.

[21] Appl. No.: 804,381

[22] Filed: Jun. 7, 1977

[51] Int. Cl.$^2$ ............................................. G01N 33/16
[52] U.S. Cl. ................................................... 23/230 B
[58] Field of Search ........................... 23/230 B; 424/12

[56] References Cited

U.S. PATENT DOCUMENTS

| | | | |
|---|---|---|---|
| 2,770,602 | 11/1956 | Weichselbaum | 23/230 B X |
| 3,171,783 | 3/1965 | Fisk | 424/12 |
| 3,438,737 | 4/1969 | Atkinson et al. | 23/253 TP X |
| 3,485,587 | 12/1969 | Keston | 23/230 B |
| 3,874,794 | 4/1975 | Schmitt et al. | 23/230 B X |
| 4,038,031 | 7/1977 | Lam | 23/230 B |

OTHER PUBLICATIONS

Malloy et al., J. Biol. Chem. 119, 481 (1937).
Richterich, R., Chemical Chemistry Theory & Practice, S. Karger, Basel, Switzerland, 1969, pp. 419–425.

Primary Examiner—Robert M. Reese
Attorney, Agent, or Firm—Morgan, Finnegan, Pine, Foley & Lee

[57] ABSTRACT

Reagent and reagent mixtures useful for detecting and measuring total bilirubin concentrations in biological liquids such as serum and methods of assaying biological liquids using such reagents are disclosed.

9 Claims, No Drawings

TOTAL BILIRUBIN ASSAY

BACKGROUND OF THE INVENTION

This invention relates generally to a novel assay method. More particularly, it relates to an assay method for the detection of total bilirubin in serum and other body fluids.

Bilirubin is present in biological liquids in different molecular forms, generally divided however into two types, i.e., conjugated and non-conjugated. Assay methods have been devised for detection of conjugated bilirubin, also referred to as direct bilirubin as well as for total bilirubin which includes both the conjugated and non-conjugated forms. Detection of the latter comprises the subject matter of this invention.

Total bilirubin is usually measured in blood serum by means of a diazo reaction in which bilirubin which has been liberated from the protein to which it is bound is reacted with a diazonium salt which leads to the formation of a dypyrrole pigment.

The prior art methods of assaying total bilirubin have numerous shortcomings. For instance, the diazonium salt reagent used in the diazotization reaction is unstable and it is particularly difficult to store either in reconstituted or lyophilized condition. Another common and frequent problem deals with the turbidity problem one encounters when adding the biological liquid to previously used reagents. Such turbidity interferes with the measurement of total bilirubin giving questionable results.

It is the objective of the herein disclosed invention to provide a bi-reagent total bilirubin procedure which can be used in wet or lyophilized chemistry formulations involving a singular reaction effected concurrently or sequentially.

It is a further objective to provide a procedure for assaying total bilirubin in a sample under conditions which overcome the aforedescribed stability and turbidity problems associated with prior art techniques.

SUMMARY OF THE INVENTION

Accordingly, this invention relates to a method for quantitatively determining the total bilirubin concentration in a biological liquid which comprises treating a measured amount of a biological liquid, such as a blood serum sample, under alkaline conditions, reacting the liberated bilirubin from the biological liquid with a stabilized diazo reagent and spectrophotometrically measuring absorbance of the resulting mixture at about 600 mu.

The treatment and reaction steps are carried out using reagents stored separately prior to analysis in reconstituted or lyophilized condition. The assay method proceeds in a sequential or simultaneous manner. Sequential means the sample is combined with one of the reagents followed by admixing with the other reagent. Simultaneous means the combined reagents are admixed with sample. In both instances, the system can be automated or non-automated.

In either case, once the reagents are combined with the sample to be tested, the method proceeds efficiently and provides highly accurate results.

DETAILED DESCRIPTION OF THE INVENTION

As a result of automation of assay methods in the diagnostic area, it has become increasingly more important to be able to run a diagnostic test procedure in which the results are accurate, the reagents or material used during assay are relatively stable whether in the wet or dry state, and where there is a minimum of complicating factors of the type described above.

In the present invention where the assay is for total bilirubin, there is a bi- or two-reagent system involved in the assay: one chemistry involves the solubilization of the biological liquid sample and the second chemistry involves a diazotization reaction. The ingredients which comprise the solubilizing and diazotizing reagent materials are preferably in lyophilized condition prior to testing. Before the test is run however these reagent materials are reconstituted generally at or about the same time the sample is added. Upon introduction of sample, solubilization and diazotization take place either sequentially or simultaneously. The reaction mixture is subsequently spectrophotometrically measured for the resulting chromogen at or about 600 mu whose absorbance is proportional to the amount of bilirubin present in the test sample.

In the present invention whether in an automated or non-automated system and irrespective of the sequence of steps, the sample is solubilized using a solubilizing reagent which acts to solubilize the albumin bound bilirubin under alkaline conditions.

If the sequential analysis procedure is followed, the solubilization of albumin bound bilirubin in the sample is effected in two stages. In the first stage, the sample to be tested is combined with a buffering agent such that the pH of the resulting mixture is in the range from 10.5 to 13.5. A preferred buffering system for purposes of this invention is one comprised of sodium hydroxide and glycine.

The amount of sodium hydroxide in this buffering reagent, when reconstituted, is from about 4 to about 10 g/100 ml and the glycine component, correspondingly, is from about 4 to about 10 g/100 ml. Potassium hydroxide, in equivalent amounts, can be substituted for sodium hydroxide.

In addition to assisting in solubilizing the albumin-bound bilirubin, the buffering agent of the type described above serves to accelerate the diazonium coupling reaction which occurs on addition of the diazo reagent and it aids in stabilizing the resulting azobilirubin chromophore.

In the second stage, i.e. where the diazo reagent is combined, diphylline is included in the second reagent which additionally assists in solubilizing the liberated bilirubin. Dyphylline is present in the second reagent in amounts, on reconstitution, of from about 2 to about 10 g/100 ml.

While dyphylline is most preferred as the solubilizing ingredient, other solubilizing agents, although less preferred, can be used in its place. Caffeine for instance or surfactants such as acetyl pyridium chloride, sodium lauryl sulfate, etc. are acceptable for purposes of this invention. The only requirement of these less preferred agents is that they permit or allow total release of albumin-bound bilirubin present in the biological fluid under the conditions specified.

If these substitute materials are used, corresponding equivalent amounts thereof are used in place of dyphylline.

The other ingredients in the diazo reagent relate to the formation and stabilization of diazo compound. A preferred composition comprises sulfanilic acid present, in reconstituted form, in amounts of from about 0.1 to about 1 g/100 ml, sodium nitrite present, in reconstituted form, in amounts of from about 5 to about 100 mg/100 ml and maleic acid present, in reconstituted form, in an amount sufficient to stabilize the diazotizing component, i.e., the reaction product of sulfanilic acid and sodium nitrite and to permit the aforesaid reaction to take place under acidic conditions.

Maleic acid is the preferred material for purposes of this invention since it can be lyophilized together with the other ingredients of the diazo reagent without any untoward side reactions.

Acceptable substitutes for maleic acid for wet use include HCl, $HNO_3$, $H_2SO_4$ or any other acid which provides sufficient acidity so as to permit the aforedescribed diazotization reaction to occur and to lend stabilization to the resulting diazo component.

Concerning the diazo reagent, diazotized sulfanilic acid which results from the formation of sulfanilic acid and sodium nitrite has been found to be most preferred for this invention. However, substitutes for sulfanilic acid include 2,4-dichloroaniline, sulfathiazole, sulfadiazine, sulfamethazine, sulfamerazine as well as other substituted sulfonamides at equivalent molar concentrations.

Sodium nitrite can of course be substituted for by any suitable $NO_2$-generating material which permits formation of the diazo reagent.

The spectral determination using the above compositions is typically measured in the region 500–700 mu, the maximum corresponding proportionately to the amount of bilirubin in the sample.

Reconstruction of the diazo containing reagent will result in an acidic pH, i.e., in the range from 1 to 5. The acidity is necessary, as stated earlier, to allow the diazotization reaction to occur and such will take place immediately upon reconstitution of the lyophilized reagent.

Once the solubilized sample is combined and mixed, the pH of the resulting reaction mixture will be in the range from about 11 to about 13.5.

In the simultaneous system, the reagents are reconstituted from a lyophilized condition or prepared in the wet state. Sample to be tested is then combined with the reagents and the assay carried out.

EXAMPLE I

A diagnostic reagent composition illustrating the present invention is outlined hereinbelow:

1. Place 8.0 grams of sodium hydroxide in a 100 ml volumetric flask, add 60 ml of distilled water, dissolve. Cool reagent to room temperature, adjust volume using distilled water to the 100 ml mark. To this mixture add 8.0 grams glycine, mix until all solids are dissolved.

2. Place 3.0 grams of maleic acid, and 0.310 grams of sulfanilic acid in a 100 ml volumetric flask, add 80.0 ml of distilled water and mix, until all solids are dissolved. Then adjust the volume by adding distilled water to the 100 ml mark. In another 100 ml volumetric flask, add 16.0 mg of sodium nitrite, add distilled water to the 100 ml mark and mix until all the solids are dissolved.

3. In a 150 ml beaker, place 6.0 grams of dyphylline. To this add 50 ml of the reagent above (#2) containing the maleic acid, sulfanilic acid and mix. Stir until all solids are dissolved. Then add 50.0 ml of the reagent containing the sodium nitrite, mix until the reagent looks clear. Transfer the solution to a dark flask.

4. Combine 1.5 ml of Reagent 1 and 1.5 ml of Reagent 3. Add 0.1 ml of serum and mix. Incubate for 5 minutes at 25° C–37° C. The absorbance of this reaction is then measured at 600 mu in any spectrophotometer. This method is linear to 30 mg/dl of total bilirubin as a function of absorbance.

Also, both reagents (#1 and #2) can be lyophilized by conventional means to create a dry reagent preparation. This dry reagent is stable and only requires the addition of water to create an active preparation for the assay of total bilirubin.

The above procedure illustrates a non-automated, simultaneous assay method.

EXAMPLE II

The procedure of Example I can be accomplished sequentially with equivalent results as follows:

Reagents 1 and 2, in lyophilized form, are contained in a cell wherein the compartment holding reagent 1 is also an optical cell. Sample is added to the compartment containing reagent 1 while simultaneously reconstituting reagent 2. Thereafter the ingredients in the two compartments intermix and the total bilirubin is determined by spectrally measuring the optical cell container at about 600 mu.

It should be understood by those skilled in the art that various modifications may be made in the present invention without departing from the spirit and scope thereof as described in the specification and defined in the appended claims.

What is claimed is:

1. A method for quantitatively determining the total bilirubin concentration in a bilirubin-containing biological liquid which comprises at least partially solubilizing a measured amount of said biological liquid under alkaline conditions, reacting the liberated bilirubin from said biological liquid with a stabilized diazo reagent under said alkaline conditions and spectrophotometrically measuring absorbance of the resulting solubilized mixture.

2. The method of claim 1 wherein said spectrophotometric measurement is read at about 600 mu.

3. The method of claim 1 wherein said treatment and reaction steps are carried out simultaneously.

4. The method of claim 1 wherein said mixture containing said biological liquid is rendered solubilized by the combined effect of sodium hydroxide, glycine and dyphylline.

5. The method of claim 1 wherein the reagents used to effect said partial solubilization and said reaction are maintained under lyophilized conditions prior to use.

6. The method of claim 1 wherein the reagents used to effect said partial solubilization and said reaction are reconstituted just prior to use in said partial solubilization and reaction steps.

7. The method of claim 1 wherein said treatment and reaction steps are carried out sequentially.

8. The method of claim 7 wherein said partial solubilization step comprises treating a measured amount of said biological liquid with a mixture comprised of sodium hydroxide and glycine, and said reaction step comprises mixing said partially solubilized liquid with a mixture comprised of sulfanilic acid, sodium nitrite, maleic acid and dyphylline.

9. The method of claim 8 wherein said partial solubilization and reaction mixtures are in lyophilized form.

* * * * *